(12) United States Patent
Ten Kate et al.

(10) Patent No.: US 11,272,863 B2
(45) Date of Patent: Mar. 15, 2022

(54) MONITORING ACTIVITY OF A SUBJECT

(71) Applicant: KONINKLIJKE PHILIPS N.V., Eindhoven (NL)

(72) Inventors: Warner Rudolph Theophile Ten Kate, Waalre (NL); Jozef Hubertus Gelissen, Herten (NL); Doortje Van De Wouw, Eindhoven (NL)

(73) Assignee: Koninklljke Philips N.V., Eindhoven (NL)

( * ) Notice: Subject to any disclaimer, the term of this patent is extended or adjusted under 35 U.S.C. 154(b) by 0 days.

(21) Appl. No.: 16/761,845

(22) PCT Filed: Nov. 16, 2018

(86) PCT No.: PCT/EP2018/081640
§ 371 (c)(1),
(2) Date: May 6, 2020

(87) PCT Pub. No.: WO2019/101656
PCT Pub. Date: May 31, 2019

(65) Prior Publication Data
US 2021/0196153 A1 Jul. 1, 2021

(30) Foreign Application Priority Data
Nov. 22, 2017 (EP) ..................................... 17202977

(51) Int. Cl.
*A61B 5/11* (2006.01)
*G08B 21/04* (2006.01)
(Continued)

(52) U.S. Cl.
CPC ........... *A61B 5/1124* (2013.01); *A61B 5/1118* (2013.01); *A61B 5/1123* (2013.01);
(Continued)

(58) Field of Classification Search
CPC ... A61B 5/1124; A61B 5/1118; A61B 5/1123; A61B 5/1126
See application file for complete search history.

(56) References Cited

U.S. PATENT DOCUMENTS 9,641,991 B2 5/2017 Pitis
2014/0278229 A1* 9/2014 Hong ..................... A61B 5/486
702/160

(Continued)

FOREIGN PATENT DOCUMENTS

WO 2017071988 A1 5/2017

OTHER PUBLICATIONS

International Search Report and Written Opinion, International Application No. PCT/EP2018/081640, dated Jan. 3, 2019.
(Continued)

*Primary Examiner* — Eric F Winakur

(57) ABSTRACT

A concept for monitoring a subject employs: a first sensor output signal representative of detected air pressure; and a second sensor output signal representative of a detected property of at least one of: the subject; and the environment. A dressing activity of the subject is determined based on the first sensor output signal and the second sensor output signal. Information about a dressing activity of the subject may, for example, be useful for the purpose of assessing the subject's physical and/or mental abilities.

15 Claims, 3 Drawing Sheets

(51) Int. Cl.
*G16H 50/30* (2018.01)
*A61B 5/00* (2006.01)
(52) U.S. Cl.
CPC .......... *A61B 5/1126* (2013.01); *A61B 5/7275* (2013.01); *A61B 5/7282* (2013.01); *A61B 5/742* (2013.01); *A61B 5/746* (2013.01); *G08B 21/0423* (2013.01); *G16H 50/30* (2018.01); *A61B 2560/0257* (2013.01); *A61B 2560/0431* (2013.01)

(56) References Cited

U.S. PATENT DOCUMENTS

| | | |
|---|---|---|
| 2016/0278706 A1 | 9/2016 | Okamoto et al. |
| 2017/0014089 A1 | 1/2017 | Murakami et al. |
| 2017/0119283 A1 | 5/2017 | Ten Kate et al. |

OTHER PUBLICATIONS

Matic, A. et al., "Monitoring Dressing Activity Failures Through RFID and Video", Methods of Information in Medicine, vol. 51, No. 1, Jan. 2012.

Gokalp, H. et al., "Monitoring Activities of Daily Living of the Elderly and the Potential for Its Use in Telecare and Telehealth: A Review", Telemedicine and E-Health, vol. 19, No. 12, Oct. 2013.

\* cited by examiner

MONITORING ACTIVITY OF A SUBJECT

CROSS-REFERENCE TO PRIOR APPLICATIONS

This application is the U.S. National Phase application under 35 U.S.C. § 371 of International Application No. PCT/EP2018/081640, filed on 16 Nov. 2018, which claims the benefit of European Patent Application No. 17202977.9, filed on 22 Nov. 2017. These applications are hereby incorporated by reference herein.

FIELD OF THE INVENTION

This invention relates to monitoring activity of a subject and in particular to monitoring dressing activity of a subject.

BACKGROUND OF THE INVENTION

Assessment or monitoring of a subject's health status, physical abilities, mental abilities, or recuperation after injury, hospitalization and treatment is of primary concern in many branches of medicine, including geriatrics, rehabilitation and physical therapy, neurology and orthopaedics, nursing and elder care.

Investigations have found that an individual's functional ability is actually environment-specific, since function increases when subjects are in familiar surroundings due to reduced confusion. Also, one-time assessment of function does not allow for assessment of variability of functional performance over the course of a day or several days, nor does it allow for assessment of change which is important in determining the adequacy of certain clinical services and treatments (such as rehabilitation) following functional loss.

A consensus therefore exists that it is preferable to assess or monitor independent functioning of a subject at their home or within familiar surroundings.

A level of independent function is commonly indicated by the quality in which Activities of Daily Living (ADLs) are performed. ADLs refer to the most common activities that people perform during a day. Therefore, a reduced quality in the ADLs can be an indicator for care needed. For example, an anomaly in the regular performance of one or more ADLs can serve as warning for special attention.

Devices and systems have been developed to monitor the ADLs of individuals as they live independently in their own home or within familiar surroundings. For example, one such known system for detecting activities of daily living of a subject system comprises three main components: (i) a sensor system that collects information about the subject's activities and behaviours; (ii) an intelligence (or information processing) system that interprets the sensor signals for determination of ADL behaviour; and (iii) a user interface system that enables care givers to inspect the interpreted (processed) information. The intelligence system typically makes use of computational techniques known in the art as artificial intelligence.

In practice, however, a major difficulty is encountered by the wide range of variations that can happen in actual care cases. Since there are so many possible circumstances, situations, environment layouts and contexts that can occur in daily life, it is common to employ numerous sensors in an attempt to capture enough information about a subject's activities and/or environment to enable identification of specific activities. This, however, typically increases complexity and/or costs and may therefore be undesirable.

An ADL that has been proposed to be potentially useful for monitoring a subject is the activity of dressing (and/or undressing). For example, it has been proposed that the activity of dressing may provide useful information about a behaviour of the monitored subject, and irregularities in dressing (or undressing) activity may indicate that some form of assistance, help of supervision may be needed. Also, timing of dressing (or undressing) activity may be indicative of a health status.

However, no adequate approaches to monitoring dressing activity of a subject currently exist. For example, one currently proposed approach employs Radio Frequency IDentification (RFID) tags attached to items of clothing, but this requires such tags to be washable and applied to numerous different items of clothing. Furthermore, an RFID reader is required to detect that the subject is dressing/undressing with items of clothing having such RFID tags, and this should exclude other activities with the items of clothing (such as washing or ironing for example). Another proposed approach relies on capturing and processing images/video of the monitored subject, but this may be highly intrusive and limited to specific locations.

SUMMARY OF THE INVENTION

The invention aims to at least partly fulfil the aforementioned needs. To this end, the invention provides devices, systems and methods as defined in the independent claims. The dependent claims provide advantageous embodiments.

There is provided a system for monitoring activity of a subject within an environment. The system comprises a signal interface adapted to receive: a first sensor output signal representative of detected air pressure; and a second sensor output signal representative of a detected property of at least one of: the subject; and the environment. The system also comprises a monitor unit adapted to determine a dressing activity of the subject based on the first sensor output signal and the second sensor output signal.

There is provided a system for monitoring activity of a subject within an environment. The system comprises: a signal interface adapted to receive: a first sensor output signal representative of detected air pressure within a surrounding of the subject, wherein the first sensor output signal is provided by a first sensor adapted to be worn or carried by the subject; and a second sensor output signal representative of a detected property of at least one of: the subject; and the environment; and a monitor unit adapted to determine a dressing activity of the subject based on the first sensor output signal and the second sensor output signal.

Embodiments may be based on the insight that a dressing activity of a subject (such as get dressed or undressed) may be determined by monitoring air pressure in the vicinity of the subject. By detecting a sudden change in air pressure at a body part of the subject, it may be inferred that the subject is dressing (or undressing). This inference may be confirmed or qualified by a signal from a secondary sensor such as a light sensor, accelerometer or other sensor that may detect a change in a parameter of the subject or surrounding environment which is indicative of the change in air pressure being caused by a dressing (or undressing) activity of the subject. A dressing activity of a subject may therefore be detected or inferred from concurrent changes in signals from two different sensors. Dressing activity may, for example, encompass a dressing activity that involves putting on one or more items of clothing and an undressing activity that involves taking off one or more items of clothing. Thus, reference to a dressing activity should be understood as referring to a dressing activity or an undressing activity. For example, when putting on a coat, or doing some other dressing, the movement of the subject's wrist through a sleeve may be detected by the combined occurrence of both a (short) increase in detected air pressure at the subject's wrist and a (short) drop in detected light intensity at the subject's wrist. For this purpose, a wrist-worn device comprising an air pressure sensor and light sensor may be provided and worn on the monitored subject's wrist. The co-occurrence of changes in two sensor signals thus enable the dressing event to be distinguished from temporary pressure or light changes resulting from other (non-dressing activity) actions. Such dressing activity may be useful as a general metric for monitoring a subject. Combination of signals from two or more sensors may thus raise specificity. For instance, a short pressure rise may be indicative of sleeve movement (implying high sensitivity), but might also be due to some other cause (implying low specificity). For example, closing a door is known to induce a short rise of air pressure, and may thus be confused as a sleeve movement. A similar account holds for a light sensor. Closing a door does not affect the light sensor. Combination of such signals may thus provide high sensitivity and high specificity.

Purely by way of example, a proposed embodiment may comprises a wearable device that has two sensors: (i) an air pressure sensor and (ii) a supplementary sensor (such as a light-sensitive sensor or accelerometer). For instance, the wearable device may be a wrist-worn device having a first (air-pressure) sensor and a second (light-sensitive) sensor. Signals from the first sensor may be monitored to identify a sudden change (e.g. rise) in air pressure. Signals from the second sensor may be monitored for a sudden change (e.g. drop) in light intensity. Concurrent changes (e.g. changes occurring at approximately the same time or within a predetermined window time) may be detected and an output signal indicative of the concurrent changes can then be generated.

Thus, rather than employing numerous and/or complex sensor arrangements and attempting to process complicated sensor data, proposed embodiments may use simple signals from, firstly, an air pressure sensor and, secondly, a supplementary sensor for monitoring a parameter of the subject or surrounding environment (i.e. two sensors). One or more of such sensors may already be present for other purposes including intruder detection or other forms of ADL monitoring for example. Embodiments may therefore be implemented in conjunction with pre-existing, pre-installed or otherwise separately-provisioned sensors, and the output signals from such sensors may be received and processed in accordance with proposed concepts. Other embodiments may be provided with sensors (e.g. where appropriate sensors are not already available). For instance, a system according to an embodiment may comprise: the first sensor adapted to detect an air pressure within a surrounding of the subject and to generate the first sensor output signal representative of the detected air pressure; and the second sensor adapted to detect a value of a property of at least one of: the subject; and the environment and to generate the second sensor output signal representative of the detected property. Embodiments may therefore include the sensors required to determine dressing activity, and thus be provided as stand-alone systems. This may provide the benefit of not needing to function, interact and/or communicate with pre-existing sensors. Proprietary and/or tailored systems that are optimised for purpose may thus be provided.

By way of example, the second sensor may comprise at least one of: a camera; a radar system; a touch-sensitive surface (e.g. a smartwatch or smart phone screen); a WiFi signal detection system; a pyroelectric infrared (PIR) sensor; a global positioning system; a light sensor; a temperature sensor; an acceleration sensor (e.g. for detecting movement or swinging of a body part); a magnetic field sensor (e.g. for detecting magnets or ferromagnetics in an item of clothing); a RFID sensing arrangement (e.g. for detecting location of a subject); pressure sensor (e.g. for detecting location of a subject); and a triboelectric sensor (e.g. for detecting contact or friction). Embodiments may therefore be adapted to employ signals from conventional sensors that are widely available, and which may be already provided as part of existing ADL monitoring systems. Existing sensors may thus be leveraged to provide new and improved functionality relating to detecting and monitoring dressing activity of a subject.

Based on the timing of changes, switches or transitions in the sensor signals, embodiments may determine (e.g. infer) information about a dressing activity of a subject without relying on complex and/or expensive sensor arrangements, thus reducing costs.

Information regarding the physical and/or mental health of a subject may be inferred from dressing activities determined from an air pressure sensor and supplementary sensor (s) (which may, for example, be worn or carried by the subject). For instance, a first sensor may be positioned so as to detect the sudden pressure change at an ankle or leg of a subject, and a second sensor may be positioned so as to detect the light intensity at the ankle or leg of the subject. As the subject puts on a pair of trousers, a concurrent change in air pressure and light intensity may be determined from the signals from the first and second sensors. Based on the simultaneous or synchronised sensed changes in air pressure and light intensity, it may be inferred that the subject is dressing (e.g. putting on trousers). In this way, no additional sensors and/or monitors (such a RFID sensors, or video capture devices, etc.) may be required in order to determine a dressing activity of the subject. Also, in some embodiments it may not be required to know or assume the exact form of dressing activity. Instead, it may suffice to simply observe the occurrence of dressing activity or transition time) since such occurrences may be monitored in order to detect a variation (e.g. increase or decrease in frequency) and from which a change in dressing activities may be inferred. This may also provide the advantage of reduced complexity.

Embodiments may thus provide information on the dressing activities of a subject in a non-intrusive manner (e.g. without requiring a video camera system). Such information about dressing activities of a subject may be useful for the purpose of assessing the subject's physical and/or mental abilities. For example, adherence to pattern or schedule of dressing has been reported to be a general/summary indicator of health, wherein unexpected and/or unusual dressing activity may be indicative of mental or physical issues.

By way of example, embodiments may be extended to providing information on dressing activity for several occurrences. A matrix or table of dressing times may therefore be built, and this may be used to monitor dressing activity over extended periods of time with improved accuracy and/or flexibility.

The monitor unit may be adapted to determine a dressing activity of the subject based on a comparison of timings of changes in detected values represented by first and second sensor output signals.

For this purpose, the sensor output signals may comprise a timestamp or other time-indicative value which may be used to indicate the associated time at which values (or changes in values) are sensed/detected. This may have the advantage of catering for any delays in transmission or reception of the signals from the sensors.

In some embodiments, the signal interface may be further adapted to receive a third sensor output signal representative of a detected further property of at least one of: the subject; and the environment. Also, the monitor unit may then be further adapted to determine supplementary information relating to the determined dressing activity of the subject based on the third sensor output signal. The third sensor output signal may, for example, be used to provide further information about determined dressing activity. Such additional information may also be used to qualify or refine the determined dressing activity. For instance, a signal from a temperature sensor indicative of a drop in detected temperature may be used to infer that the subject has put on an item of outerwear (such as a coat) and ventured outside (due to the detection of a sudden drop in temperature). By way of further example, a signal from a PIR sensor may be used to identify that the subject is within a specific room or area, and from this an item of clothing may be inferred (e.g. detection of dressing activity in a bedroom may imply normal clothing like a shirt, blouse or trousers, whereas detection of dressing activity in a hallway may imply an item of outwear such as a coat).

In proposed embodiments, the monitor unit may be further adapted to determine a trend or pattern in the dressing activity of the subject based on the determined dressing activity of the subject and historical data relating to one or more previously determined dressing activities of the subject.

Thus, there may be proposed a concept of monitoring a physical or mental capability of a subject by identifying a trend in the subject's dressing activity. By using a currently sensed or determined dressing activity, along with previously determined dressing activities, a trend, pattern, change or drift of the dressing activity (or a property thereof) may be identified. For example, by detecting a consistent change or pattern in detected dressing activity over time, a trend in a subject's dressing activities (and thus physical or mental capability) may be inferred and, from this, current and/or future care/help/assistance requirements may be determined. Thus, there may be proposed a concept of determining a trend in a subject's capability or activity based on current and historical dressing activity. For instance, a determined pattern of dressing activity of the subject may be used to infer a physical or mental capability of a subject, and this may be undertaken numerous times over an extended time period (such as hours, days, weeks, months or years) so as to enable monitoring of the subject's physical or mental capability over time.

A trend in the physical and/or mental capability of a subject may therefore be inferred without employing a complex and/or expensive sensor arrangement within a monitored environment. This may help to reduce associated cost and/or complexity of a monitoring system. For example, embodiments may alleviate a need to employs RFID tags in items of clothing and arrange the RFID sensors in dedicated or exact locations. For instance, rather than focussing on obtaining an exact or accurate measurements for a single instance of dressing activity, embodiments may instead observe a trend or pattern in the occurrences of dressing activity.

Embodiments may therefore enable the monitoring of a subject's physical capability by analysing the timing of detected occurrences of dressing activity and inferring a trend or pattern in detected occurrences. For instance, the times of (un)dressing may be stored in a time series. The times may be assessed to see if they are "normal", where normal can be user dependent. For example, a period of time during the day may be identified as being when the subject normally dresses and/or undresses. The detected dressing activities may thus be checked to see if they occur within that time interval. Similarly, when no occurrence of dressing activity is detected within the predetermined time interval, an alert signal may be generated for indicating expected dressing activity has not been detected.

In some embodiments, the monitor unit may be further adapted to detect an irregularity or anomaly in the determined trend or pattern. For example, the monitor unit may be adapted to detect an irregularity based on a comparison of a determined trend or pattern with a threshold value. For example, this may provide the advantage that an alarm may be given if the subject dresses at an unusual time, or fails to dress at, on or before/after an expected time (and potentially in conjunction with other activities like bathing or eating, for example), indicating that, for example, the subject has become unwell. By way of example, in some embodiments, the threshold value may be determined based on at least one of: one or more previously determined occurrences of dressing activity of the subject; and one or more previously determined changes in values of the dressing activity of the subject.

To detect an irregularity or anomaly, the monitor unit may undertake a comparison of the determined trend with a threshold value. For example, the monitor unit may employ a data processing unit that compares the determined trend with a threshold value and then generates an alert signal if the determined trend exceeds the threshold value. The threshold may be pre-programmed and fixed, but it may be preferable to enable the threshold value to be set by a user preference.

Embodiments may, for instance, facilitate the detection of a potential wandering of the subject and such a detected event may be used to raise an alert (e.g. to a career or medical professional). Subjects suffering mental (cognitive) decline, for example because they are affected by Alzeheimer's Disease, may leave the home unaccompanied. Because of their disease, such wandering might be unwanted if not supervised. Therefore, proposed embodiments may address a need for detecting wandering (e.g. leaving the house). For instance, detecting dressing activity, such as putting on the coat, may be used as characteristic indicative of wandering for a wandering detection system.

Embodiments may further comprise a user input interface adapted to receive a user input for defining or modifying one or more alert conditions, and the monitor unit may be adapted to generate an alert output signal based on the determined trend or pattern and the one or more alert conditions.

Further, the threshold may be based on previously determined values of dressing activity of the subject and/or a previously determined trend or pattern in dressing activity of the subject. For instance, the threshold value may be determined based on at least one of: one or more previously detected values of the dressing activity of the subject; and one or more previously determined changes in values of the dressing activity of the subject. In other words, the threshold may be defined by taking account of a history of detected values and/or a history of changes in values of the dressing activity so that it can be used to identify outlying values or anomalies.

In a further embodiment of the system, the monitor unit may be further adapted to store the determined dressing activity of the subject in an activity database. Previously determined values may therefore be stored, in a historical database for example, and then used in subsequent calculations. Furthermore, a currently determined dressing activity may be used to re-calculate or refine a previously determined trend or pattern.

Thus, a pattern of the dressing activity of the subject may be stored. Shifts in this pattern may indicate that the subject is in need of help. For example, the subject may start to dress later than normal due to increased physical difficulties, and this may be inferred from a trend in dressing time of the monitored subject.

The monitor unit may be further adapted to detect an irregularity or anomaly in the activity database. For example, by adding time/date information to the determined instances of dressing activity, the duration between the determined instances may be determined. With the time/date information, the frequency or timing of the dressing activity may be determined. For example, the frequency of the dressing activity may be 'two times a day', or '14 times a week'. An irregularity in the activity database may then, for example, be that a frequency of the dressing activity has decreased (or increased) significantly. For example, the average number of times instances of dressing activity occur may be determined using the data from the activity profile. When the number of occurrences of dressing activity is less the average this indicates an irregularity.

In a further embodiment, the monitor unit may be further arranged to generate a warning signal in response to a detected irregularity. The irregularity may indicate that the subject is in need of help and/or advise the subject to start doing exercises to improve physical condition for example. In a further example, a medical practitioner, a caregiver, a family member or close relative may be advised by the system (using the alert signal) to pay a visit to the subject. In a further embodiment the warning signal may be provided to the subject himself/herself. For example, the warning signal may be a feedback signal advising the subject to take a certain medication.

Embodiments may be adapted to provide a generated alert or warning signal to at least one of: the subject; a medical practitioner; and a caregiver.

An embodiment may be further adapted to generate a display control signal for modifying a graphical element based on the determined dressing activity of the subject, and the system may further comprise: a display system adapted to display the graphical element in accordance with the generated display control signal. In this way, a user (such as a care giver) may have an appropriately arranged display system that can receive and display information about a determined dressing activity of the monitored subject, and that subject may be remotely located from the user. Embodiments may therefore enable a user to remotely monitor a subject using a portable display device, such as a laptop, tablet computer, mobile phone, PDA, etc.

It will be appreciated that all or part of a system according to an embodiment may comprise one or more data/signal processing units. For example, the monitor unit may be implemented using a single processor which is adapted to undertake data processing in order to determine a dressing activity of the subject (based on the signals from two sensors). The signal processing unit may be remotely located from the sensors, and signals issued by the sensors may be communicated to the signal processing unit via respective communication links.

The system may further comprise: a server device comprising the monitor unit. Dedicated data/signal processing means may therefore be employed for the purpose of determining a dressing activity of the subject, thus reducing processing requirements or capabilities of other components or devices of the system.

The system may further comprise a client device, wherein the client device comprises the monitor unit and a display system. In other words, a user (such as a care giver) may have an appropriately arranged client device (such as a laptop, tablet computer, mobile phone, PDA, etc.) which processes received sensor signals in order to determine a dressing activity of the subject.

Thus, processing may be hosted at a different location from where the sensor signals are generated or issued. For example, for reasons of power efficiency (e.g. to improve battery lifetime) it might be advantageous to execute only part of the processing at the sensor location(s), thereby reducing associated costs, processing power, transmission requirements, etc.

Embodiments may also enable some of the processing load to be distributed throughout the system. For example, pre-processing may be undertaken at a sensor system. Alternatively, or additionally, processing could be undertaken at a communication gateway. In some embodiments, processing may be undertaken at a remote gateway or sever, thus relinquishing processing requirements from an end-user or output device. Such distribution of processing and/or hardware may allow for improved maintenance abilities (e.g. by centralising complex or expensive hardware in a preferred location). It may also enable computational load and/or traffic to be designed or located within a networked system according to the processing capabilities available. A preferable approach may be to process sensor signals locally and transmit extracted data for full processing at a remote server.

Thus, it will be understood that processing capabilities may be distributed throughout the system in different ways according to predetermined constraints and/or availability of processing resources.

According to another aspect of the invention, there is provided a method for monitoring activity of a subject within an environment. The method comprises: obtaining a first sensor output signal representative of detected air pressure; obtaining a second sensor output signal representative of a detected property of at least one of: the subject; and the environment; and determining a dressing activity of the subject based on the first sensor output signal and the second sensor output signal.

According to an aspect of the invention, there is provided a method for monitoring activity of a subject within an environment. The method comprises: obtaining a first sensor output signal representative of detected air pressure within a surrounding of the subject, wherein the first sensor output signal is provided by a first sensor adapted to be worn or carried by the subject; obtaining a second sensor output signal representative of a detected property of at least one of: the subject; and the environment; and determining a dressing activity of the subject based on the first sensor output signal and the second sensor output signal.

The non-intrusive character of the detecting and/or monitoring a subject's dressing activity may be realized by analysing the timing of changes or transitions in signals from two sensors. A change or transition in a signal from a first air pressure sensor may for example indicate a subject putting on a garment or item of clothing. This may then be coupled with a change or transition in a signal from a second sensor that detects incident light, movement and/or contact at a body part of the subject, and which may therefore provide information as to an action or activity of the subject. The timings of the changes/transitions in the first and second signals may be analysed to determine if they are linked and indicative of a dressing activity.

In an embodiment, the step of determining a dressing activity of the subject may comprise comparing timings of changes in detected values represented by first and second sensor output signals.

According to yet another aspect of the invention, there is provided a computer program product, wherein the computer program product comprises a computer-readable storage medium having computer-readable program code embodied therewith, the computer-readable program code configured to perform all of the steps of a proposed embodiment.

In an embodiment, a computer system may be provided which comprises: a computer program product according to an embodiment; and one or more processors adapted to perform a method according to an embodiment by execution of the computer-readable program code of said computer program product.

In a further aspect the invention relates to a computer-readable non-transitory storage medium comprising instructions which, when executed by a processing device, execute the steps of a method for monitoring an activity of a subject according to an embodiment.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying drawings, in which.

DETAILED DESCRIPTION OF THE EMBODIMENTS

Figure 1A:
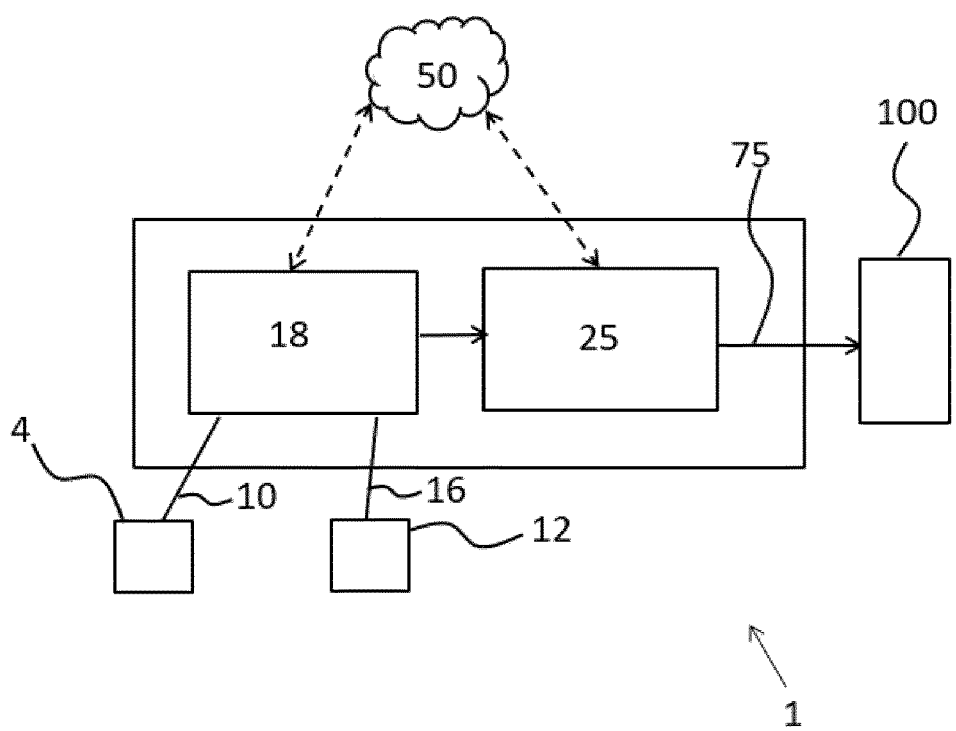
FIG. 1A is a simplified block diagram of a system for monitoring activity of a subject within an environment according to an embodiment.

Proposed is a concept for detecting and/or monitoring dressing activity of a subject within an environment, which may be useful for the purpose of unobtrusively monitoring the well-being of the subject for example. Such subjects may, for instance, include a disabled subject, an elderly subject, an injured subject, a medical patient, a person, etc. Elderly subjects can mean subjects above 50 years, above 65 years, above 70, or above 80 years old, for example.

Illustrative embodiments may be utilized in many different types of monitoring environments, such as a hospital, ward, care home, subject's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented.

It has been recognized that, in many care situations, there is often a need to be informed about the ADLs a subject is performing. There may also be a need to be alerted when an anomaly occurs. The type of anomaly can be different per case. A large class of anomalies relate to aberrations in an ADL routine of the subject. For example, an above average number of toilet visits during the night. More severe incidents form another class, for example falls by the subject. Further refined algorithms may also be needed when a (declining) trend in activity is to be detected.

Embodiments of the present invention are therefore directed toward enabling an ADL of a subject to be detected and/or monitored, and more particularly to enabling dressing activity of a subject to be detected and/or monitored. This may be used to generate an alert signal for an alerting or warning system that can indicate the subject is in need of help, for example.

Embodiments are based on the insight that detection of a sudden change in air pressure at (or near) a body part of a subject combined with concurrent detection of a change in a parameter of the subject or surrounding environment can be used to infer a dressing activity of the subject. Furthermore, from such dressing activity, the subject's health or wellbeing may be assessed and/or monitored. Thus, instead of employing RFID tags, video cameras and/or movement sensors and attempting to implement complex or computationally-intensive calculations on sensor data, proposed embodiments may obtain (e.g. receive) simple signals directly from an air pressure detector and a supplementary sensors (such as a light sensor or accelerometer) and then analyse such signals to determine a dressing activity of a subject. By using simple signals obtained from two detectors, embodiments may determine (e.g. infer) information about the physical well-being of a subject without relying on complex and/or expensive sensor arrangements, thus reducing costs.

Proposed is a concept of inferring the dressing activity of a subject from the timing of changes or transitions in signals from an air pressure sensor and supplementary sensor. For example, a change in a signal from a first (air pressure) sensor worn on a wrist of a subject may indicate a change in circumstances at the subject's arm. This may then be combined with a change or transition in a signal from a second (light) sensor also worn on the wrist of the user indicating the subject's arm has been covered. The time elapsed between the changes/transitions in the signals from the first and second sensors may be used to determine if they are linked, associated or concurrent, and this may then be used to infer whether or not the signal's changes/transitions have been caused by the subject putting on an item of clothing.

Embodiments thus propose the use of the timings of detections from an air pressure sensor and a supplementary sensor. An elapsed time between transitions/changes of the first and second sensors may be used to infer a dressing activity of a subject. Such a proposed speed inference system/method may therefore be employed in a system for monitoring a subject within an environment.

FIG. 1A shows an embodiment of a system 1 for monitoring activity of a subject in an environment (such as a home for example) according to an embodiment.

In this example, the system 1 includes a first sensor 4 adapted to detect air pressure at a body part of the subject and to generate a first sensor output signal 10 representative of the detected air pressure. The system 1 also includes a second sensor 12 adapted to detect the intensity of light incident on the body part of the subject 6 and to generate a second sensor output signal 16 representative of the detected intensity of incident light.

The first 4 and second 12 sensors communicate their respective sensor output signals 10, 16 to a signal interface 18 of the system 1 via wired or wireless connections. The signal interface 18 is thus adapted to receive sensor output signals 10, 16 from the first 4 and second 12 sensors via one or more appropriately arranged communication links. By way of example, the wireless connections may comprise a short-to-medium-range communication link. For the avoidance of doubt, short-to-medium-range communication link should be taken to mean a short-range or medium-range communication link having a range of up to around 100 meters. In short-range communication links designed for very short communication distances, signals typically travel from a few centimetres to several meters, whereas, in medium-range communication links designed for short to medium communication distances, signals typically travel up to 100 meters. Examples of short-range wireless communication links are ANT+, Bluetooth, Bluetooth low energy, IEEE 802.15.4, ISA100a, Infrared (IrDA), ISM Band, Near Field Communication (NFC), RFID, 6LoWPAN, UWB, Wireless HART, Wireless HD, Wireless USB, ZigBee. Examples of medium-range communication links include Wi-Fi, Z-Wave.

The signal interface 18 is thus adapted to receive the first 10 and second 16 sensor output signals via one or more appropriately arranged communication links. Thus, it will be appreciated that the signal interface 18 may be remotely located from the monitored subject. In such an arrangement, the sensor signals 10, 16 can be transferred to a local gateway, which processes and/or transmits the sensor signals to the remotely located signal interface (e.g. using wired or wireless transmission, including cellular phone).

The signal interface 18 passes the received sensor output signals 10, 16 to a monitor unit 25 of the system 1. The monitor unit 25 is adapted to determine a dressing activity of the subject based on the first sensor output signal 10 and the second sensor output signal 16. More specifically, the monitor unit 25 determines a dressing activity of the subject by comparing the timings of changes in detected values represented by first and second sensor output signals 10, 16.

Figure 1B:
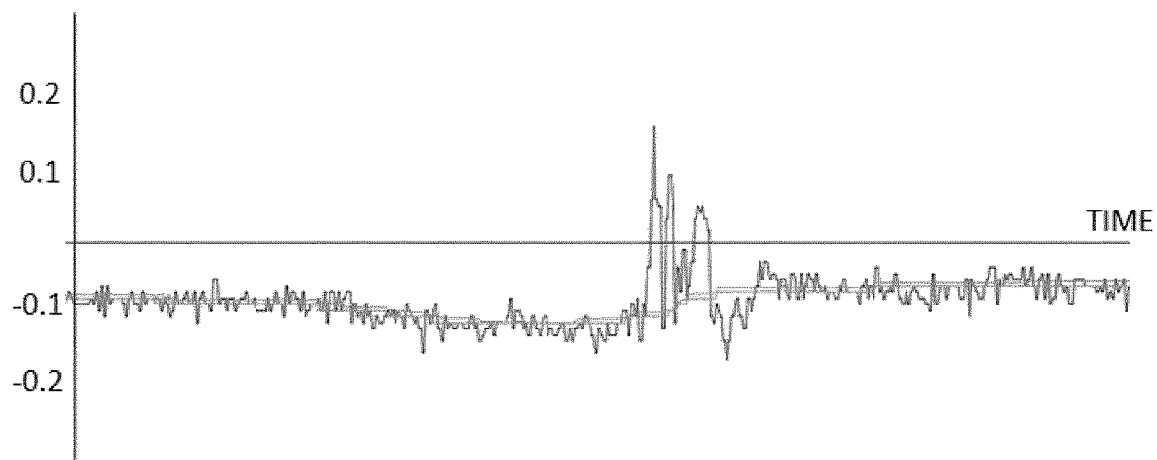
FIG. 1B illustrates a graph depicting a variation in detected air pressure versus time for a time period containing an instance of the subject putting on a coat.

By way of example, one may consider the subject putting on a coat. In such an example, as the subject puts on the coat, he/she puts his/her wrist into a sleeve of the coat and subsequently moves his/her wrist through the longitudinal extent of the sleeve. In doing so, the first sensor output signal 10 will indicate a sudden change (e.g. brief increase) in detected air pressure as the wrist enters the sleeve of the coat. For example, FIG. 1B illustrates a graph depicting a variation in detected air pressure (as represented by the first sensor output signal) versus time for a time period containing an instance of the subject putting on a coat (e.g. the subject's wrist moves through the sleeve).

Also, the second sensor output signal 16 will concurrently and subsequently indicate a change (e.g. decrease) in detected light intensity as the wrist moves along the inside of the sleeve.

More specifically, the monitor unit 25 may determine the time elapsed between:

(i) the first sensor output signal 10 from the first sensor 4 indicating a change in detected air pressure; and (ii) the second sensor output signal 16 from the second sensor 12 indicating a change in detected light intensity.

Here, it is noted that, if one defines the elapsed time to relate to the time elapsed from the time that the first sensor output signal changes/transitions until the time that the second sensor output signal changes/transitions, the transition time may have a negative value for the example where light intensity drops shortly before an increase in air pressure is detected. Put another way, with the elapsed time being defined with respect to a particular order (e.g. from first sensor output signal to second sensor output signal), an obtained time may have a negative value. Thus, depending on configuration of the sensors and the direction in which time difference between signals is defined, the time may have a positive or negative value. The order of signal changes may thus depend on whether the dressing activity comprises putting on an item of clothing or taking off an item of clothing. The order may also depend on way the sensors are mounted. In addition, multiple light sensors might be mounted; one 'upstream', the other 'downstream', and the order in their responses (e.g. changes or transitions) may enable determination of the distinction between a dressing or undressing activity (e.g. between putting on an item of clothing or taking off an item of clothing). Using a plurality of light sensors may result in more similar response signals such that the temporal order can be determined more robustly.

The value of time elapsed between the indication of changes in the signals from the first 10 and second 16 sensor output signals may then be analysed in order to determine a dressing activity of the subject. The monitor unit 25 is thus adapted to determine a dressing activity of the subject based on the timing of changes in the first 10 and second 16 sensor output signals. For this purpose, the monitor unit 25 may communicate with one or more data processing resources available in the internet or "cloud" 50. Such data processing resources may undertake part or all of the processing required to infer or determine a dressing activity of the subject based on the obtained timings of transitions in the sensor output signals. Thus, the embodiment may employ distributed processing principles.

The monitor 25 is further adapted to generate an output signal 75 representative of determined dressing activity of the monitored subject. In other words, after determining a dressing activity of the monitored subject 6 (based on the obtained output signals 10,16 from the first 4 and second 12 sensors, either with or without communicating with data processing resources via the internet or "cloud"), an output signal 75 representative of a determined dressing activity of the subject is generated.

The system further comprises a graphical user interface (GUI) 100 for providing information to one or more users. The output signal 75 is provided to the GUI 100 via wired or wireless connection. By way of example, the wireless connection may comprise a short-to-medium-range communication link. As indicated in FIG. 1A, the output signal 75 is provided to the GUI 100 from the monitor unit 25. However, where the system, has made use of data processing resources via the internet or cloud 50, an output signal may be made available to the GUI 100 via the internet or cloud 50.

Based on the output signal 75, the GUI 100 is adapted to communicate information by displaying one or more graphical elements in a display area of the GUI 100. In this way, the system may communicate information about a dressing activity of the monitored subject that may be useful for indicating that the subject is in need of attention or for estimating when the subject may be expected to require assistance or attention. For example, the GUI 100 may be used to display graphical elements to a medical practitioner, a caregiver, a family member or close relative. Alternatively, or in addition, the GUI 100 may be adapted to display graphical elements to the monitored subject 6.

Thus, the dressing activity of the subject 6 may be inferred from the relative timing of changes or transitions in the signals from first 4 and second 12 sensors. Put another way, it is proposed to obtain and analyse signals from two sensors. Since such sensors may be small or comprise sensors that may be provided in a wearable housing/support (such as a device adapted to be worn on a wrist or ankle of a subject), embodiments may be completely unobtrusive. Embodiments may also be adapted to facilitate other functions, such as time, fall detection, activity measuring, heart rate measuring, respiration rate, communication (smart watch), etc. The monitored subject may thus need only undertake their normal activities and may not even be aware that their dressing activity movement is being detected and/or monitored.

Although, in the embodiment of FIGS. 1A and 1B, the second sensor 12 has been described as being adapted to detect the intensity of light incident on the body part of the subject, it is to be understood that, in other embodiments, other or additional sensors may be employed. For example, the second sensor may comprise an accelerometer for monitoring wrist/arm movement and providing movement information that may be analysed to confirm that the detected movement is typical of putting on a coat. Conversely, an accelerometer may be provided as a third sensor which provides a third, alternative modality, for example to compensate in cases where the wrist worn device is covered by a sleeve and the light sensor signal exhibits a smaller change in output when putting on a coat.

Furthermore, a third sensor may be employed for detecting a further property of at least one of: the subject. Supplementary information relating to a determined dressing activity of the subject may then be based on an output signal from such a third sensor.

For instance, where the first sensor comprises an air pressure detector and the second sensor comprises a light sensor, a third sensor comprising an accelerometer arrangement may be used to measure walking activity (or other activity recognition functions). These features can be used to combine with the coat-on detection to further improve the detection and classification accuracy. For example, a detected coat-on event followed by an accelerometer signal representative of walking may lead to the inference that the subject is wandering. Alternatively, or additionally, coat-on detection can be used to improve other activity recognition functions.

Another sensor that may be employed by embodiments is a triboelectric sensor. A triboelectric sensor may be adapted to respond to touch and moving (e.g. rubbing) contact between the sensor (e.g. on a wrist device) and a garment (e.g. sleeve). The polarity and strength of this static electricity may differ according to the material, from which information about the type of garment may be inferred.

Yet another sensor that may be employed is a temperature sensor. A temperature sensor may be adapted to measure a drop in environmental temperature, and thus provide information that may confirm the subject has put on a coat and is now walking outside (e.g. with a sudden drop of temperature being associated with the subject venturing outside to a cold environment).

Other parameters that may be detected and leveraged to provide information about dressing activity include Wi-fi signal strength and GPS location.

From the above description of the embodiment of FIG. 1, it will be understood that there is proposed a system which analyses the relative timings of transitions in signals from an air pressure sensor and a supplementary sensor so as to determine a dressing activity of a monitored subject. This may be thought of as providing dressing activity detection and/or monitoring on a short term timescale (for example, at real-time). Such implementations may, for example, detect current dressing activity. For instance, if the monitored subject is determined to be undertaking dressing/undressing at an unusual time, an alert signal may be provided to caregiver. Also, embodiments may be adapted to request that the monitored subject acknowledges the alert before an alert signal is provided to the caregiver (so as to provide an opportunity for the subject to indicate the alarm is a false alarm for example).

Other embodiments, however, may provide dressing activity detection and/or monitoring on a long term timescale (e.g. for pattern recognition and trend determination). Such implementations may, for example, obtain information about dressing activities of the subject, e.g. activity/movement levels or patterns. Also, deviations from usual patterns or trends may be detected and translated into an alert or alarm. Such deviations may relate to incidental deviations (e.g. user did not undress during the night) or indicate gradually increasing deviations (e.g. indication of cognitive decline or physical decline).

Thus, some embodiments may further comprise a monitor unit adapted to determine a trend in a capability or activity of the subject based on a determined dressing activity and historical data relating to previously determined transition dressing activities of the subject.

Accordingly, proposed is a concept for monitoring a subject by determining a trend or pattern in the dressing activities of the subject.

In general, to be able to observe trends in "normal" daily behaviour of a subject one may monitor the dressing activities of a subject. From established trends or patterns, one may also spot unexpected activities, anomalies or deviations from expected values or patterns. The type of anomaly or irregularity can be different per case.

A large class of physical or mental capabilities can relate to an ADL routine of the subject. For example, a physical capability may be inferred from the speed by which a subject dresses. Also, the dressing activities may provide a measurement of total physical effort, which can be useful for monitoring purposes. Embodiments of the present invention may therefore be directed toward enabling information about a physical or mental capability of a subject to be obtained and potentially monitored. Such information may therefore be useful for monitoring the health or well-being of a subject.

Some embodiments can employ a concept of determining a trend in a (physical or mental) capability or activity of a subject from a currently sensed or determined dressing activity of the subject and historical data relating to one or more previously detected dressing activities of the subject. In other words, determination of a trend in a capability or activity of a subject may be based on current and previously detected dressing activities of the subject. Such a proposed concept for monitoring a physical or mental capability or activity of a subject may therefore be employed in a system for monitoring ADLs of a subject within an environment.

For the purpose of such long-term monitoring and/or trend identification, determined transition times (and associated values) may be stored in a database adapted to store historical data relating to one or more previously detected dressing activities. In doing so, each determined dressing activity instance/occurrence may be labelled with a timestamp identifying when the dressing activity was detected. In the trend determination or analysis, the detected values may then be averaged per time unit, e.g. per day or per day portion, before the trend is estimated. Also, given a (known) context, one may also choose to exclude or include certain days. For example, on Fridays, the grandchildren or a cleaning lady are in the house and so detected values may not be representative of the monitored subject.

Another approach may be to provide each detected dressing activity instance/occurrence as a pair of time/date and dressing activity value, so that trend analysis, using a regression method for example, may account for the varying rate (e.g. irregularity in arrival) at which values are detected.

By storing previous detected transition time values, estimates of a trend in the transition times may be determined and a future date/time at which the subject may require help or assistance may be identified (e.g. by extrapolating the trend to identify when it goes above/below a threshold value). Furthermore, currently detected dressing activities may be used to re-calculate or refine previously determined trends (e.g. those stored in a database for example). Further, embodiments may be self-learning (e.g. using machine learning algorithms) by using previously detected values.

By detecting dressing activity based on relative timings of changes or transitions or changes in signals from multiple sensors, a trend in the detected dressing activity over time may be identified and, from such a trend, a capability or activity of a subject may be monitored. For example, a trend of increasing decreasing dressing speed may be used to identify and monitor a trend in the subject's physical or cognitive abilities.

Figure 2:
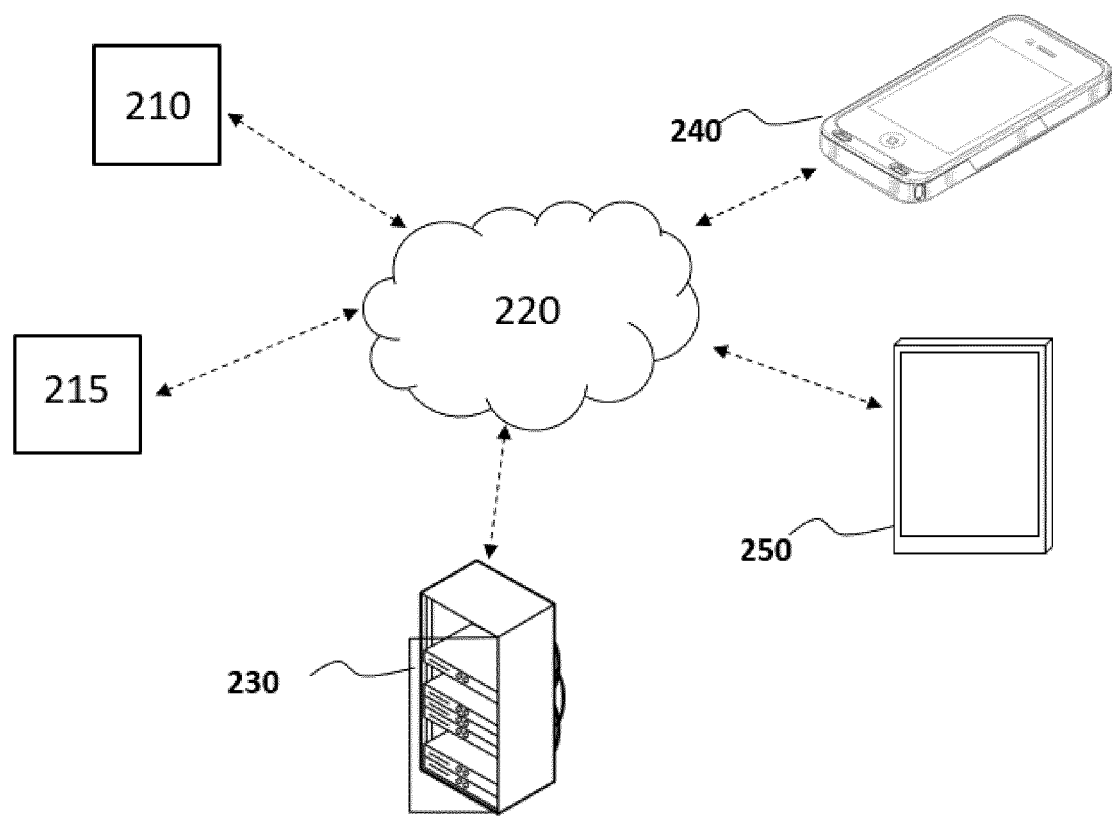
FIG. 2 is a simplified block diagram of a system for monitoring a subject according to another embodiment.

Referring now to FIG. 2, there is depicted another embodiment of a system according to the invention comprising first 210 and second 215 sensors. Here, the first sensor 210 is adapted to detect air pressure at an ankle of a subject and to generate a first sensor output signal representative of the detected air pressure. The second sensor 215 comprises an a triboelectric sensor adapted to detect rubbing or contact of an item against the ankle of the subject and to generate a second sensor output signal representative of the detected rubbing/contact.

The first 210 and second 215 sensors are each adapted to communicate their respective sensor output signals via the internet 220 (using a wired or wireless connection for example) to a remotely located monitoring system 230 (such as server).

The monitoring system 230 is adapted to receive the sensor output signals from the first 210 and second 215 sensors and process the received sensor output signals in accordance with a timing detection algorithm in order to determine a value of time elapsed between a significant change in air pressure represented by the first sensor output signal and a change in ankle rubbing or contact represented by the second sensor output signal. Based on the determined value of elapsed time, the monitoring system then determines a dressing activity of the subject.

The monitoring system 230 is further adapted to processes the current dressing activity of the subject in combination with historical data relating to one or more previously determined dressing activities of the subject to determine a trend in the dressing activities over time. The trend can be found as a linear line (e.g., using linear regression), but may also be curved using higher order fitting techniques.

The monitoring system 230 is further adapted to generate output signals representative of inferred or calculated dressing activity trend. Thus, the monitoring system 230 provides a centrally accessible processing resource that can receive information from the sensors 210, 215 and run one or more algorithms to transform the received information into a description of a trend in a dressing activity of the subject.

Previously determined dressing activities (and associated information, such as time, date, description, etc.) may therefore be stored, in a historical database for example, and then used in subsequent calculations. Furthermore, currently detected dressing activity may be used to re-calculate or refine a previously determined trend. Thus, the pattern of dressing activity of the subject may be stored. Shifts in this pattern may indicate that the subject is in need of help. For example, the subject may start forgetting to dress or undress, and this may be inferred from a trend in a frequency of dressing activity.

Further, the monitoring system 230 is adapted to detect an irregularity in the historical database. For example, by adding time information to the determined dressing activity, the time spent between the dressing/undressing occurrences may be determined. With the time information, the frequency of the dressing/undressing activity may be determined.

Such provision of information about a detected or inferred dressing activity trend and/or irregularity may be undertaken in response to a receiving a request (via the internet 220 for example) and/or may be undertaken without request (i.e. 'pushed').

For the purpose of receiving information about a detected dressing activity trend from the monitoring system, and thus to enable the subject to be monitored, the system further comprises first 240 and second 250 mobile computing devices.

Here, the first mobile computing device 240 is a mobile telephone device (such as a smartphone) with a display for displaying graphical elements representative of a subject's physical or mental well-being. The second mobile computing device 250 is a mobile computer such as a Laptop or Tablet computer with a display for displaying graphical elements representative of a subject's dressing activity.

The monitoring system 230 is adapted to communicate output signals to the first 240 and second 250 mobile computing devices via the internet 220 (using a wired or wireless connection for example). As mentioned above, this may be undertaken in response to receiving a request from the first 240 or second 250 mobile computing devices.

Based on the received output signals, the first 240 and second 250 mobile computing devices are adapted to display one or more graphical elements in a display area provided by their respective display. For this purpose, the first 240 and second 250 mobile computing devices each comprise a software application for processing, decrypting and/or interpreting received output signals in order to determine how to display graphical elements. Thus, the first 240 and second 250 mobile computing devices each comprise a processing arrangement adapted to one or more values representative of a trend, and to generate a display control signal for modifying at least one of the size, shape, position, orientation, pulsation or colour of the graphical element based on the one or more values representative of trend.

The system can therefore communicate information about a detected dressing activity of a monitored subject to users of the first 240 and second 250 mobile computing devices. For example, each of the first 240 and second 250 mobile computing devices may be used to display graphical elements to a medical practitioner, a caregiver, a family member or close relative. Also, the system can generate a warning signal in response to a detected irregularity. The irregularity may, for example, indicate that the subject is in need of help and thus a generated alert or warning signal may be provided to at least one of: the subject; a medical practitioner; and a caregiver.

Implementations of the system of FIG. 2 may vary between: (i) a situation where the monitoring system 230 communicates display-ready dressing activity data, which may for example comprise display data including graphical elements (e.g. in JPEG or other image formats) that are simply displayed to a user of a mobile computing device using conventional image or webpage display (which can be web based browser etc.); to (ii) a situation where the monitoring system 230 communicates raw data set information that the receiving mobile computing device then processes to determine a dressing activity of a subject, and then displays graphical elements based on the determined dressing activity (for example, using local software running on the mobile computing device). Of course, in other implementations, the processing may be shared between the monitoring system 230 and a receiving mobile computing device such that part of the data generated at monitoring system 230 is sent to the mobile computing device for further processing by local dedicated software of the mobile computing device. Embodiments may therefore employ server-side processing, client-side processing, or any combination thereof.

Further, where the monitoring system 230 does not 'push' information (e.g. output signals), but rather communicates information in response to receiving a request, the user of a device making such a request may be required to confirm or authenticate identity and/or security credentials in order for the information to be communicated.

Figure 3:
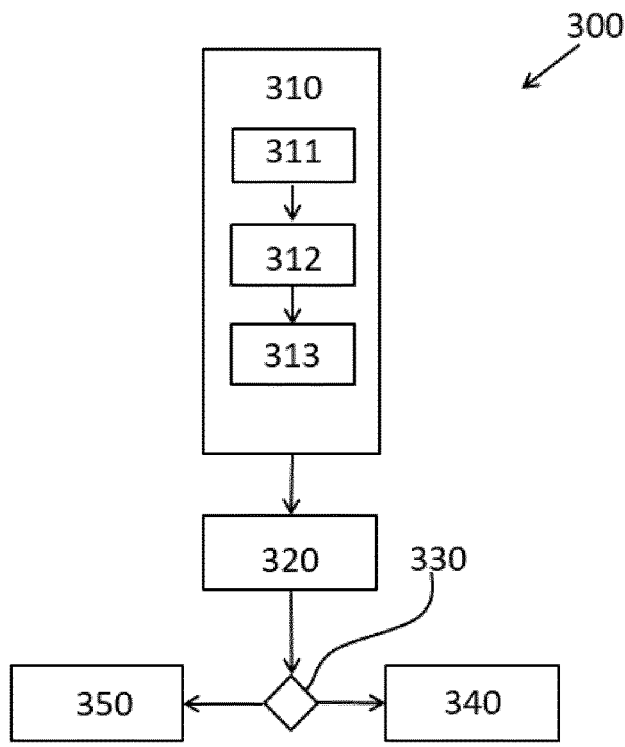
FIG. 3 is a flow diagram of a method for monitoring a subject according to an embodiment.

Referring now to FIG. 3, there is shown a flow diagram of an exemplary method 300 for monitoring a subject.

The method begins with step 310 in which a dressing activity of the subject is detected. Specifically, the step 310 of detecting a dressing activity of a subject comprises the sub-steps of: obtaining 311 a first sensor output signal representative of detected air pressure; Obtaining 312 a second sensor output signal representative of a detected property of at least one of: the subject; and the environment; and determining 313 a dressing activity of the subject based on the first sensor output signal and the second sensor output signal.

Next, in step 320, a trend in dressing activity of the subject is determined based on the current dressing activity of the subject that was determined in step 310 and historical data relating to one or more previously detected dressing activities (of the monitored subject).

Then, in step 330, the determined trend is compared with a predetermined threshold value. The threshold value can be pre-programmed, fixed or dynamically set in response to calculations based on one or more previously obtained dressing activities (e.g. using trend analysis), but is preferably also enabled to be set by a user preference. Thus, the threshold may be based on previously determined values representative of a physical or mental capability the subject. In other words, the threshold may be defined by taking account of a history of the subject and/or taking account of previous calculations so that it can be used to identify outlying values or anomalies.

If, in step 330, the trend is determined to exceed the first threshold value, the method proceeds to step 340 wherein a warning signal is generated and output along with information describing the trend and/or the detected dressing activity. If, in step 330, the trend is determined to not exceed the first threshold value, the method proceeds to step 350 wherein the information describing the detected dressing activity is output and/or stored without any warning signal.

Here, it is noted that in alternative embodiments, step 330 may also perform another test procedure. This may bypass the trend computation in step 320.

From the above description of the method illustrated by FIG. 3, it will be understood that proposed embodiments may be adapted to detect an irregularity in a determined trend. For example, in the embodiment of FIG. 3, the steps of 330 to 350 may be implemented by a monitor unit and be implemented to detect an irregularity based on a comparison of a determined trend with a threshold value. This may provide the advantage that an alarm or alert signal may be generated and communicated when an irregularity or anomaly is detected (e.g. if the subject fails to get undressed, indicating that the subject may have become too unwell/weak). In this example, to detect an irregularity, the monitor unit undertakes a relatively simple comparison of the determined trend with a threshold value. The threshold may be preprogramed and fixed, but it may be preferable to enable the threshold value to be set by a user preference. This may identify when a threshold value may be exceeded in the future, for example.

Other methods to detect outliers or to detect changes in a time series are known in the art. By way of example, in an embodiment, the monitor unit may be further adapted to calculate an estimated future value of the property based on the determined trend, and the monitor unit may be further arranged to detect an irregularity based on a comparison of the estimated future value of the property with a threshold value and to generate an alert output signal in response to the detected irregularity. A threshold value may thus relate to a future value, and a determined trend may be extrapolated for comparison of an extrapolated value with the future threshold value. Using the extrapolated trend, one may estimate the time until the trend will cross the threshold, and provide that number as an identification of when intervention or assistance may be required, for example. In another embodiment, the trend may simply be displayed to user and left for visual inspection (e.g. for the purpose of identifying outliers or changes in a trend).

Purely by way of example, one or more steps of the method 300 for monitoring a physical or mental capability of a subject may be implemented in a portable computing device (such as the smartphone or portable computer shown in FIG. 2) in order to control the display of graphical elements on a display. Of course, it will be understood that proposed embodiments for monitoring a subject's dressing activity may be implemented in other methods and/or systems.

Embodiments may further comprise a control unit adapted to generate one or more control signals for the control system based on the determined dressing activity. In this way, embodiments may be adapted to provide control signals that are suitable for use by a control system. Accordingly, rather than just monitoring dressing activity of a subject, some embodiments may be adapted to operate a control system so as to assist the subject. For example, if dressing activity is detected, and if it happens in low light, an embodiment may communicate a control signal to the control system which causes the control system to change or improve the lighting conditions (e.g. automatically switch on the light in the room).

It is also noted that, although it has been described above that embodiments need not employ additional/supplementary sensors, some embodiments may further comprise a sensor adapted to detect a value of a property of at least one of: the environment, control/operation of an object, and the monitored subject. Such a supplementary sensor arrangement may help to improve the accuracy of dressing activity determination for example. Supplementary sensor readings may, for instance, qualify or refine data analysis undertaken by the signal processing unit and/or the monitor unit.

By way of further example, for wandering detection, embodiments may be adapted to detect that a subject has been putting on a coat. A first wandering detection/inference concept may be based on identifying that the dressing action happens outside the "normal" times, or during the suspected times the subject may start wandering. Abnormal times could for instance be at night or set specifically per subject (e.g. by a caregiver). A further concept may be based on detecting a "coat-on" dressing activity is shortly followed by a door-open event (e.g. by using an open-close sensor for sensing opening/closing of the front door). Alternatively, a detection of having put-on the coat may be used to set a corresponding state and the door-open event (not necessarily shortly afterwards) may cause an alert (labelled with higher urgency) when this (coat-on) state is set.

Embodiments may be provided in the form of a wearable device, such as a bracelet, wrist strap, ankle strap, smartwatch, etc., so as to detect a subject's dressing activity without the subject needing to intentionally or consciously activate/operate the sensors. In this way, a subject may only need to undertake their normal activities. Such strategic positioning may ensure that dressing activity of the subject can be automatically and accurately detected, and this may not require the subject to remember to undertake any special or additional activities in order for a value to be detected by the sensor(s). This may remove the risk of the subject forgetting to activate a sensor (e.g. by pressing a button), for example.

When such a body-worn system is used in combination with an existing ADL monitoring system, information can be combined to give more detailed information about the dressing activity (e.g. where the subject is (un)dressing). For example, if dressing activity happens in the hallway, it is more likely to be putting on a coat. If it is in the bedroom, it is more likely to be normal clothing like a shirt, sweater or blouse.

Further, embodiments may employs pairs of sensors, for example, one pair at one end of a forearm (e.g. at the hand end of a forearm) and another pair at the other end (e.g. at the elbow end of the forearm). By doing so, it may be determined whether the user is putting on or taking off an item of clothing. For example, when putting on clothing, the sensors closer to the hand will respond shortly before the sensors at the elbow end. Another approach may be to space the first and second sensors apart so as to enable a direction of dressing to be inferred. This may, however, require some training of the algorithm(s) so that the differences in timing between the combined signals can be classified by the algorithm in either direction of movement (e.g. putting on or taking off an item of clothing).

In addition, to measure if the subject is dressing, embodiments may be adapted to measure if several pieces of clothes are put on top of each other (several output signals, possibly of decreasing strengths, in the same direction). Also, embodiments may be able to identify if a shirt with long or short sleeves has been put on based on the output pattern and duration of the signals and a training mechanism of the algorithm.

There exist many sensors that can be employed by embodiments. Typical sensors include PIR (pyroelectric infrared sensor; detect movement and presence), temperature sensors, light sensors, friction sensors or pressure sensors. Many others exist and are conceivable.

The sensors may also be adapted to undertake primary processing of the detected values, such a signal filtering, sampling, conditioning, etc., so as to reduce a required transmission bandwidth and/or transmission duration for example.

Non-intrusive monitoring may therefore be realized with relatively simple sensors that provide data on specific properties of the subject (such as movement, for example). Also, the dressing activity of the subject may be detected with sensors that are cheap and widely employed. Thus, embodiments may employ sensors that are considered to be non-intrusive and more easily accepted by the monitored subject. Yet, with the data provided by these sensors, a subject's dressing activity may be accurately determined and provide more information on the subject being monitored. Thus, some embodiments of the invention may employ conventional sensors and/or existing sensor arrangements. Also, embodiments may employ sensors that are considered to be non-intrusive and more easily accepted by the monitored subject.

The current description is for a device located around the wrist, which could detect (un)dressing behaviour of the upper body. A similar solution could be envisioned on other body parts like around the ankle to measure (un)dressing of the lower body (e.g. trousers).

Figure 4:
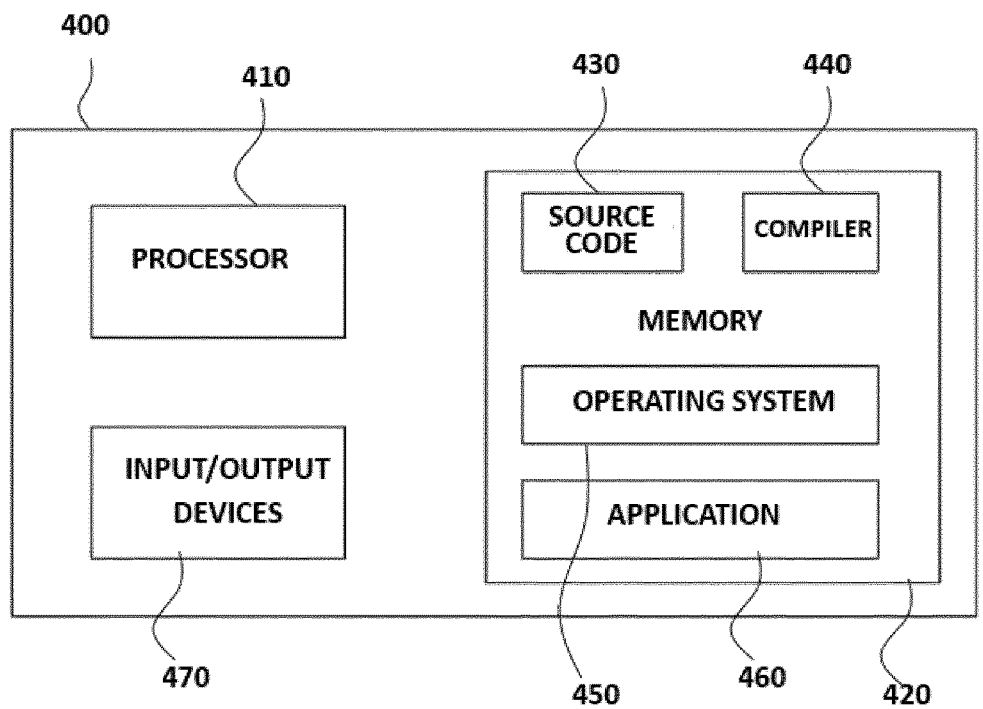
FIG. 4 is a simplified block diagram of a computer within which one or more parts of an embodiment may be employed.

FIG. 4 illustrates an example of a computer 400 within which one or more parts of an embodiment may be employed. Various operations discussed above may utilize the capabilities of the computer 400. For example, one or more parts of a monitoring system adapted to monitor a subject's dressing activity may be incorporated in any element, module, application, and/or component discussed herein.

The computer 400 includes, but is not limited to, PCs, workstations, laptops, PDAs, palm devices, servers, storages, and the like. Generally, in terms of hardware architecture, the computer 400 may include one or more processors 410, memory 420, and one or more I/O devices 470 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 410 is a hardware device for executing software that can be stored in the memory 420. The processor 410 can be virtually any custom made or commercially available processor, a central processing unit (CPU), a digital signal processor (DSP), or an auxiliary processor among several processors associated with the computer 400, and the processor 410 may be a semiconductor based microprocessor (in the form of a microchip) or a microprocessor.

The memory 420 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 420 may incorporate electronic, magnetic, optical, and/or other types of storage media. Note that the memory 420 can have a distributed architecture, where various components are situated remote from one another, but can be accessed by the processor 410.

The software in the memory 420 may include one or more separate programs, each of which comprises an ordered listing of executable instructions for implementing logical functions. The software in the memory 420 includes a suitable operating system (O/S) 450, compiler 440, source code 430, and one or more applications 460 in accordance with exemplary embodiments. As illustrated, the application 460 comprises numerous functional components for implementing the features and operations of the exemplary embodiments. The application 460 of the computer 400 may represent various applications, computational units, logic, functional units, processes, operations, virtual entities, and/or modules in accordance with exemplary embodiments, but the application 460 is not meant to be a limitation.

The operating system 450 controls the execution of other computer programs, and provides scheduling, input-output control, file and data management, memory management, and communication control and related services. It is contemplated by the inventors that the application 460 for implementing exemplary embodiments may be applicable on all commercially available operating systems.

Application 460 may be a source program, executable program (object code), script, or any other entity comprising a set of instructions to be performed. When a source program, then the program is usually translated via a compiler (such as the compiler 440), assembler, interpreter, or the like, which may or may not be included within the memory 420, so as to operate properly in connection with the O/S 450. Furthermore, the application 460 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, php. Python, ASP scripts, FORTRAN, COBOL, Perl, Java, ADA, .NET, and the like.

The I/O devices 470 may include input devices such as, for example but not limited to, a mouse, keyboard, scanner, microphone, camera, etc. Furthermore, the I/O devices 470 may also include output devices, for example but not limited to a printer, display, etc. Finally, the I/O devices 470 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 470 also include components for communicating over various networks, such as the Internet or intranet.

If the computer 400 is a PC, workstation, intelligent device or the like, the software in the memory 420 may further include a basic input output system (BIOS) (omitted for simplicity). The BIOS is a set of essential software routines that initialize and test hardware at startup, start the O/S 450, and support the transfer of data among the hardware devices. The BIOS is stored in some type of read-only-memory, such as ROM, PROM, EPROM, EEPROM or the like, so that the BIOS can be executed when the computer 400 is activated.

When the computer 400 is in operation, the processor 410 is configured to execute software stored within the memory 420, to communicate data to and from the memory 420, and to generally control operations of the computer 400 pursuant to the software. The application 460 and the O/S 450 are read, in whole or in part, by the processor 410, perhaps buffered within the processor 410, and then executed.

When the application 460 is implemented in software it should be noted that the application 460 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 460 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, optimized for embedded implementation, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to subjectalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

From the above description, it will be appreciated that embodiments propose to use two or more sensors for purposes of detecting and monitoring a dressing activity of a subject. Embodiments may therefore be useful for monitoring of elderly, disabled or unwell individuals so to support independent living. Usage data from the control system can be used both for real-time speed detection and alerts, as well as to detect gradual deviations from usual patterns or trends.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand that various embodiments with various modifications are contemplated.

The invention claimed is:

1. A system for monitoring activity of a subject within an environment, wherein the system comprises:
 a signal interface adapted to receive: a first sensor output signal representative of detected air pressure within a surrounding of the subject, wherein the first sensor output signal is provided by a first sensor adapted to be worn or carried by the subject; and a second sensor output signal representative of a detected property of at least one of: the subject and the environment wherein the second sensor output signal is provided by a second sensor; and
 a monitor adapted to:
  compare a timing of a change in the first sensor output signal that meets or exceeds a threshold value with a timing of a change in the second sensor output signal; and
  determine a dressing activity of the subject based on a time elapsed between and order of the changes in the first sensor output signal and the second sensor output signal.

2. The system of claim 1, wherein the second sensor comprises at least one of:
- a camera;
- a touch-sensitive surface;
- a radar system;
- a WiFi signal detection system;
- a pyroelectric infrared sensor;
- a global positioning system;
- a light sensor;
- a temperature sensor;
- a magnetic field sensor;
- a radio-frequency identification sensor;
- a pressure sensor;
- an acceleration sensor; and
- a triboelectric sensor.

3. The system of claim 1, wherein the signal interface is further adapted to receive a third sensor output signal representative of a detected further property of at least one of: the subject and the environment,
and wherein the monitor is further adapted to determine supplementary information relating to the determined dressing activity of the subject based on the third sensor output signal.

4. The system of claim 1, further comprising:
the first sensor adapted to detect an air pressure within the surrounding of the subject and to generate the first sensor output signal representative of the detected air pressure; and
the second sensor adapted to detect a value of the property of at least one of: the subject and the environment and to generate the second sensor output signal representative of the detected property.

5. The system of claim 1, wherein the monitor is further adapted to determine a trend or pattern in the dressing activity of the subject based on the determined dressing activity of the subject and historical data relating to one or more previously determined dressing activities of the subject.

6. The system of claim 5, wherein the monitor is further adapted to detect an anomaly in the determined trend or pattern, and wherein the monitor is further arranged to generate an alert output signal in response to the detected anomaly.

7. The system of claim 1, wherein the monitor is further adapted to store the determined dressing activity of the subject in an activity database.

8. The system of claim 7, wherein the monitor is further adapted to detect an irregularity in the activity database, and wherein the monitor is further arranged to generate an alert signal in response to the detected irregularity.

9. The system of claim 7, wherein the monitor is further adapted to determine a trend or pattern in the dressing activity of the subject based on the determined dressing activity of the subject and historical data relating to one or more previously determined dressing activities of the subject, and the determined dressing activity of the subject re-calculates or refines a previously determined trend of pattern.

10. The system of claim 1, wherein the monitor is further adapted to generate a display control signal for modifying a graphical element based on the determined dressing activity of the subject,
and wherein the system further comprises:
a display system adapted to display the graphical element in accordance with the display control signal generated by the monitor.

11. A portable item adapted to be worn or carried by a subject to be monitored, the portable item comprising a housing and the system according to claim 1.

12. A system for monitoring activity of a subject within an environment, the system comprising:
a signal interface adapted to receive: a first sensor output signal representative of detected air pressure within a surrounding of the subject, wherein the first sensor output signal is provided by a first sensor adapted to be worn or carried by the subject and a second sensor output signal representative of a detected property of at least one of: the subject and the environment; and
a monitor adapted to:
determine a dressing activity of the subject based on the first sensor output signal and the second sensor output signal;
store the determined dressing activity of the subject in an activity database;
determine a frequency or timing of the dressing activity in the activity database; and
detect an irregularity or anomaly in the activity database, the detected irregularity or anomaly being dependent on a change in the determined frequency or timing of the dressing activity.

13. A method for monitoring activity of a subject within an environment, wherein the method comprises:
obtaining a first sensor output signal representative of detected air pressure within a surrounding of the subject, wherein the first sensor output signal is provided by a first sensor adapted to be worn or carried by the subject;
obtaining a second sensor output signal representative of a detected property of at least one of: the subject and the environment;
comparing a timing of a change in the first sensor output signal that meets or exceeds a threshold value with a timing of a change in the second sensor output signal; and
determining a dressing activity of the subject based on a time elapsed between and order of the changes in the first sensor output signal and the second sensor output signal.

14. A computer program product comprising a non-transitory computer readable storage medium comprising code stored thereon, which code when run on a computer implements the method of claim 13.

15. The method of claim 13, further comprising generating an alert output signal in response to determining that the dressing activity is indicative of a potential wandering of the subject.

* * * * *